(12) United States Patent
Beier et al.

(10) Patent No.: US 10,590,091 B2
(45) Date of Patent: Mar. 17, 2020

(54) PROCESS FOR THE PREPARATION OF AZIDOPERFLUOROALKANES AND N-POLYFLUOROALKYL AZIDES

(71) Applicants: Ustav organicke chemie a biochemie AV CR, v.v.i., Prague (CZ); CF Plus Chemicals s.r.o., Brno-Bohunice (CZ)

(72) Inventors: Petr Beier, Prague (CZ); Vaclav Matousek, Zliv (CZ); Zsofia E. Blastik, Budapest (HU); Svatava Voltrova, Velke Prilepy-Uholicky (CZ)

(73) Assignees: Ustav Organicke Chemie A Biochemie AV CR , v.v.i., Prague (CZ); CF Plus Chemicals s.r.o., Brno-Bohunice (CZ)

( * ) Notice: Subject to any disclaimer, the term of this patent is extended or adjusted under 35 U.S.C. 154(b) by 0 days.

(21) Appl. No.: 15/827,931

(22) Filed: Nov. 30, 2017

(65) Prior Publication Data

US 2019/0161452 A1    May 30, 2019

(51) Int. Cl.
| | |
|---|---|
| *C07D 249/04* | (2006.01) |
| *C07C 19/08* | (2006.01) |
| *C07C 247/04* | (2006.01) |
| *A01N 43/647* | (2006.01) |
| *B01J 31/18* | (2006.01) |
| *B01J 31/04* | (2006.01) |
| *C07C 323/48* | (2006.01) |
| *A61K 31/655* | (2006.01) |

(52) U.S. Cl.
CPC ........ *C07D 249/04* (2013.01); *B01J 31/1815* (2013.01); *C07C 19/08* (2013.01); *C07C 247/04* (2013.01); *C07C 323/48* (2013.01); *A01N 43/647* (2013.01); *A61K 31/655* (2013.01); *B01J 31/04* (2013.01); *B01J 2231/34* (2013.01); *B01J 2531/16* (2013.01)

(58) Field of Classification Search
None
See application file for complete search history.

(56) References Cited

PUBLICATIONS

Blastik, Zsofia E., et al., "Azidoperfluoroalkanes: Synthesis and Application in Copper(I)-Catalyzed Azide-Alkyne Cycloaddition", Wiley-VCH Verlag GmbH & Co. KGaH, Weinhem, Angew Chem. Int. Ed. 2017, 56, 346-349, published Dec. 5, 2016.

Voltrova, Svatava, et al., "Synthesis of tetrafluoroethylene- and tetrafluoroethyl-containing azides and their 1,3-dipolar cycloaddition as synthetic application", The Royal Society of Chemistry, Org. Biomol. Chem. 2017, 15, 4962-4965, published May 18, 2017.

*Primary Examiner* — Samantha L Shterengarts
(74) *Attorney, Agent, or Firm* — Notaro, Michalos & Zaccaria P.C.

(57) ABSTRACT

Process for the preparation of azidoperfluoroalkanes and azidopolyfluoroalkanes of general formula $R_F-N_3$, where $R_F$ is chosen from a group containing $C_nF_{2n+1}$, $C_nF_xH_{2n+1-x}$, $C_nF_xX_{2n+1-x}$ or $R^1CF_2CF_2$, where n is an integer in the range of 1 to 10, x is an integer in the range of 2 to 20, X is Cl, Br, or I, $R^1$ is $C_{1-10}$ alkyl, ArO, ArS, imidazolyl, benzimidazolyl, or pyrazolyl and Ar is phenyl or substituted phenyl, by the reaction of electrophilic azidation reagent of general formula $R^2-N_3$, where $R^2$ is $n-C_4F_9SO_2$, $ArSO_2$, Br, I, with synthetic equivalent of polyfluoroalkylated carbanion of general formula $[R_F]^-$.

4 Claims, No Drawings

PROCESS FOR THE PREPARATION OF AZIDOPERFLUOROALKANES AND N-POLYFLUOROALKYL AZIDES

FIELD OF THE INVENTION

The invention relates to methods of preparation of azidopolyfluoroalkanes by the reaction of synthetic equivalents of polyfluoroalkyl carbanions with electrophilic azidation reagents and to the use of azidopolyfluoroalkanes in the preparation of N-polyfluoroalkyl triazoles.

BACKGROUND ART

Organic compounds containing the trifluoromethyl group, perfluoroalkyl or polyfluoroalkyl groups find use as crop protection agents, pharmaceuticals and functional materials. In drugs, for example, the trifluoromethyl group is introduced mainly to increase metabolic stability and lipophilicity, to modulate the $pK_a$ of neighboring ionizable functional groups, and to impart weak C—F•••X interaction. Compounds with perfluoroalkyl or polyfluoroalkyl groups connected to the nitrogen atom are rare and the methods of their preparation have hardly been explored. These compounds have a high potential to display unique physico-chemical and biological properties.

Organic azides are valuable intermediates in synthetic chemistry. Their ability to react with nucleophiles or electrophiles, to access nitrene chemistry by $N_2$ elimination, or to act as dipoles in cycloadditions, underscores their versatility. The so called click reaction—Cu(I)-catalyzed azide alkyne cycloaddition (CuAAC)—is a robust, effective and selective process widely used in organic synthesis, medicinal chemistry, in the chemistry of polymers and in chemical biology. Azidotrifluoromethane ($CF_3N_3$) is a known compound, which is thermally stable up to 300° C. and it was previously prepared in two steps from trifluoronitrosomethane ($CF_3NO$) [K. O. Christe, C. J. Schack, *Inorg. Chem.* 1981, 20, 2566-2570]. The need to use not easily accessible starting materials, toxic and corrosive reagents and difficult synthesis precludes the use and investigation of properties of $CF_3N_3$. Longer carbon chain azidoperfluoroalkanes are not known, some azidopolyfluoroalkanes have been synthesized through the reaction of sodium azide with polyfluoroalkenes [C. G. Krespan, B. E. Smart, *J. Org. Chem.* 1986, 51, 320-326] or with halodifluoromethyl compounds [T. G. Archibald, K. Baum, *J. Org. Chem.* 1990, 55, 3562-3565]. In order to accelerate the development of applications and commercialization of $CF_3N_3$, azidoperfluoroalkanes and azidopolyfluoroalkanes, a more straightforward synthetic method is needed.

DISCLOSURE OF THE INVENTION

Object of the invention is a process for the preparation of azidoperfluoroalkanes and azidopolyfluoroalkanes of formula $R_F$—$N_3$,
wherein $R_F$ is selected from the group consisting of $C_nF_{2n+1}$, $C_nF_xH_{2n+1-x}$, $C_nF_xX_{2n+1-x}$ or $R^1CF_2CF_2$, wherein n is an integer in the interval from 1 to 10, x is an integer in the interval from 2 to 20 and X is Cl, Br, or I,
$R^1$ is selected from the group consisting of $C_{1-10}$ alkyl, ArO, ArS, imidazolyl, benzimidazolyl, or pyrazolyl, wherein Ar is phenyl or substituted phenyl, said process having the following steps
(A) generation of a synthetic equivalent of polyfluoroalkyl carbanion, said synthetic equivalent having the formula $[R_F]^-$, by a method selected from:
a) activation of trialkyl(polyfluoroalkyl)silane of general formula $R^3{}_3SiR_F$, wherein $R^3$ is $C_{1-5}$ alkyl, with a Lewis base which is selected from the group consisting of potassium fluoride, cesium fluoride, tetramethylammonium fluoride, tetrabutylammonium fluoride, sodium carbonate, potassium carbonate, potassium phosphate, sodium acetate, potassium acetate, tetrabutylammonium acetate;
b) reaction of polyfluoroalkane of general formula RFH with a base which is selected from a group consisting of methyllithium, butyllithium, phenyllithium, Grignard reagent of general formula $R^3MgX$, wherein $R^3$ is $C_{1-5}$ alkyl, and complexes of these compounds with LiCl;
c) reaction of halopolyfluoroalkane of general formula $R_F$Br or $R_F$I with metalation reagents, which are selected from a group consisting of methyllithium, butyllithium, Grignard reagent of general formula $R^3MgX$, wherein $R^3$ is $C_{1-5}$ alkyl, and complexes of these compounds with LiCl,
under temperature in the range from −78° C., or from the melting point of the reaction mixture, to +60° C.,
(B) reaction of an electrophilic azidation reagent of general formula $R^2$—$N_3$,
wherein $R^2$ is selected from the group consisting of n-$C_4F_9SO_2$, $ArSO_2$, Br, and I,
wherein Ar is phenyl or substituted phenyl,
with the synthetic equivalent of polyfluoroalkyl carbanion of general formula $[R_F]^-$ generated in step (A).

"Substituted phenyl" represents a phenyl substituted by at least one substitutent, preferably selected from $C_1$-$C_4$ alkyl, $C_1$-$C_4$ alkoxy, halogen, nitro, $C_1$-$C_4$ perfluoroalkyl.

In one aspect of the method, the reaction is preferably performed in the presence of at least equimolar amount of polyfluoroalkylated carbanion of general formula $[R_F]^-$ or trialkyl(polyfluoroalkyl)silane activated with a Lewis base.

In another embodiment of the method, the polyfluoroalkylated carbanion synthetic equivalents are generated from:
$CF_3SiMe_3$ or n-$C_3F_7SiMe_3$ or n-$C_8F_7SiMe_3$ activated with cesium fluoride, preferably in dimethylformamide at a temperature in the range from −60° C. to −30° C., or
$C_2F_5H$ and n-BuLi, preferably in tetrahydrofurane at a temperature in the range from −78° C. to ambient temperature, preferably up to 25° C., or
$R^1CF_2CF_2Br$ (wherein $R^1$ is as defined above) and i-PrMgCl.LiCl, preferably in tetrahydrofurane at a temperature in the range from −78° C. to ambient temperature, preferably up to 25° C.

In a preferred aspect of the method, n-$C_4F_9SO_2N_3$ or 4-($CH_3$)$C_6H_4SO_2N_3$ are used as electrophilic azidation reagents.

Preferably, the reaction is performed in an organic solvent, more preferably in a solvent selected from tetrahydrofuran and dimethylformamide.

In a preferred aspect of the method of the present invention, the products $R_F$—$N_3$ are isolated preferably by distillation, in particular when tetrahydrofuran is used as a solvent, or by distillation after addition of an organic solvent having a boiling point lower than 100° C., preferably tetrahydrofuran, in particular when dimethylformamide is used as a solvent.

A further object of the present invention is the use of compounds of general formula $R_F\text{—}N_3$ for the synthesis of N-perfluoroalkyl- or N-polyfluoroalkyl-substituted triazoles of formula 1

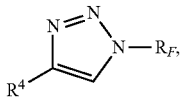

wherein $R_F$ is as defined above,
$R^4$ is selected from a group consisting of $C_{1-10}$ alkyl, $XCH_2CH_2$, $COOR^3$, $C(CH_3)_2OH$, benzyloxy-$C_{1-4}$-alkyl, pyridyl, phenyl, and pyridyl or phenyl substituted by a group selected from $C_{1-10}$ alkyl, F, Cl, Br, I, $OR^3$, $NO_2$, $NH_2$, $CF_3$,
by a cycloaddition reaction of the azide $R_F\text{—}N_3$ with alkyne of formula 2

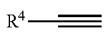

in the presence of copper(I) catalyst in at a temperature in the range from −30° C. to the boiling point of the reaction mixture.

In one aspect of the method, the reaction leading to compound of formula 1 is preferably carried out in the presence of excess of the azide $R_F\text{—}N_3$.

In another embodiment of the method, the reaction leading to compound of formula 1 is preferably carried out in the presence of a catalytic amount (for example, 2-20 mol. %, relative to the amount of the alkyne of formula 2) of copper(II) sulfate and a catalytic amount (for example, 4-40 mol. %, relative to the amount of the alkyne of formula 2) of sodium L-ascorbate or in the presence of a catalytic amount (for example, 0.5-10 mol. %, relative to the amount of the alkyne of formula 2) of copper(I) iodide or a catalytic amount (for example, 0.5-10 mol. %, relative to the amount of the alkyne of formula 2) of copper(I) 3-methylsalicylate.

In a preferred aspect of the method, the reactions leading to compound of formula 1 are preferably performed in one pot, starting from $[R_F]^-$ and $R^2\text{—}N_3$ (one-pot two-step method).

An object of the present invention is the use of compounds of formula $R_F\text{—}N_3$ for the synthesis of triazoles of general formula 3

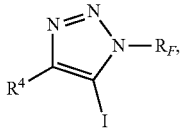

wherein $R_F$ and $R^4$ are as defined above,
by cycloaddition reaction of $R_F\text{—}N_3$ with alkyne of general formula 4

and with iodine in the presence of tertiary amine as a base, preferably selected from trimethylamine, N,N-diisopropylethylamine, N,N,N',N'-tetramethylethylenediamine, tris((1-benzyl-1H-1,2,3-triazolyl)methyl)amine or tris((1-tert-butyl-1H-1,2,3-triazolyl)methyl)amine, at a temperature in the range from −30° C. to the boiling point of the reaction mixture.

In one aspect of the method of the present invention, the reaction leading to compounds 3 is preferably performed in the presence of trimethylamine as a base at ambient temperature.

Preferably, the reactions described in the present invention are performed in an organic solvent, more preferably in a solvent selected from tetrahydrofuran and dimethylformamide.

Another object of the present invention are the following compounds prepared according to the invention:
(i) azidoperfluoroalkanes and azidopolyfluoroalkanes of formula $R_F\text{—}N_3$,
wherein $R_F$ is selected from the group consisting of $C_nF_{2n+1}$, $C_nF_xH_{2n+1-x}$, $C_nF_xX_{2n+1-x}$ or $R^1CF_2CF_2$, wherein n is an integer in the interval from 1 to 10, x is an integer in the interval from 2 to 20 and
X is Cl, Br, or I,
$R^1$ is selected from the group consisting of $C_{1-10}$ alkyl, ArO, ArS, imidazolyl, benzimidazolyl, or pyrazolyl, wherein Ar is phenyl or substituted phenyl, and wherein $R_F$ is not $CF_3$;
(ii) triazoles of formula 1

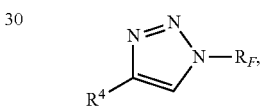

wherein $R_F$ is selected from the group consisting of $C_nF_{2n+1}$, $C_nF_xH_{2n+1-x}$, $C_nF_xX_{2n+1-x}$ or $R^1CF_2CF_2$, wherein n is an integer in the interval from 1 to 10, x is an integer in the interval from 2 to 20, and
X is Cl, Br, or I,
$R^1$ is selected from the group consisting of $C_{1-10}$ alkyl, ArO, ArS, imidazolyl, benzimidazolyl, or pyrazolyl, wherein Ar is phenyl or substituted phenyl;
$R^4$ is selected from a group consisting of $C_{1-10}$ alkyl, $XCH_2CH_2$, $COOR^3$, $C(CH_3)_2OH$, benzyloxy-$C_{1-4}$-alkyl, pyridyl, phenyl, and pyridyl or phenyl substituted by a group selected from $C_{1-10}$ alkyl, F, Cl, Br, I, $OR^3$, $NO_2$, $NH_2$, $CF_3$; wherein $R^3$ is $C_{1-5}$ alkyl;
(iii) triazoles of general formula 3

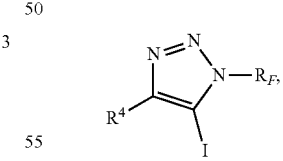

wherein $R_F$ is selected from the group consisting of $C_nF_{2n+1}$, $C_nF_xH_{2n+1-x}$, $C_nF_xX_{2n+1-x}$ or $R^1CF_2CF_2$, wherein n is an integer in the interval from 1 to 10, x is an integer in the interval from 2 to 20, and
X is Cl, Br, or I,
$R^1$ is selected from the group consisting of $C_{1-10}$ alkyl, ArO, ArS, imidazolyl, benzimidazolyl, or pyrazolyl, wherein Ar is phenyl or substituted phenyl;
$R^4$ is selected from a group consisting of $C_{1-10}$ alkyl, $XCH_2CH_2$, $COOR^3$, $C(CH_3)_2OH$, benzyloxy-$C_{1-4}$-alkyl, pyridyl, phenyl, and pyridyl or phenyl substituted by a group selected from $C_{1-10}$ alkyl, F, Cl, Br, I, $OR^3$, $NO_2$, $NH_2$, $CF_3$; wherein $R^3$ is $C_{1-5}$ alkyl.

More preferably, the compounds are selected from:
Azidopentafluoroethane,
1-Azido-1,1,2,2,3,3,3-heptafluoropropane,
1-Azido-1,1,2,2,3,3,4,4,5,5,6,6,7,7,8,8,8-heptadecafluorooctane,
(2-Azido-1,1,2,2-tetrafluoroethyl)(phenyl)sulfane,
1-(2-Azido-1,1,2,2-tetrafluoroethoxy)-4-bromobenzene,
1-(Pentafluoroethyl)-4-phenyl-H-1,2,3-triazole,
4-(4-Methoxyphenyl)-1-(pentafluoroethyl)-1H-1,2,3-triazole,
4-(2-Bromophenyl)-1-(pentafluoroethyl)-1H-1,2,3-triazole,
3-(1-(Pentafluoroethyl)-1H-1,2,3-triazol-4-yl)pyridine,
4-Phenyl-1-(trifluoromethyl)-1H-1,2,3-triazole,
4-(p-Tolyl)-1-(trifluoromethyl)-1H-1,2,3-triazole,
4-(4-Methoxyphenyl)-1-(trifluoromethyl)-1H-1,2,3-triazole,
4-(2-Bromophenyl)-1-(trifluoromethyl)-1H-1,2,3-triazole,
4-(4-Nitrophenyl)-1-(trifluoromethyl)-1H-1,2,3-triazole,
4-(1-(Trifluoromethyl)-1H-1,2,3-triazol-4-yl)aniline,
4-Butyl-1-(trifluoromethyl)-1H-1,2,3-triazole,
Ethyl 1-(trifluoromethyl)-1H-1,2,3-triazol-4-carboxylate,
2-(1-(Trifluoromethyl)-1H-1,2,3-triazol-4-yl)propan-2-ol,
(S)-4-(2-(Benzyloxy)propyl)-1-(trifluoromethyl)-1H-1,2,3-triazole,
1-(Pentafluoroethyl)-4-(p-tolyl)-1H-1,2,3-triazole,
4-(1-(Pentafluoroethyl)-1H-1,2,3-triazol-4-yl)aniline,
1-(Pentafluoroethyl)-4-(4-(trifluoromethyl)phenyl)-1H-1,2,3-triazole,
1-(Perfluoropropyl)-4-phenyl-1H-1,2,3-triazole,
1-(Perfluorooctyl)-4-phenyl-1H-1,2,3-triazole,
1-(Perfluoropropyl)-4-(p-tolyl)-1H-1,2,3-triazole,
4-(4-Methoxyphenyl)-1-(perfluorooctyl)-1H-1,2,3-triazole,
1-(Trifluoromethyl)-4-(4-(trifluoromethyl)phenyl)-1H-1,2,3-triazole,
4-(4-Fluorophenyl)-1-(trifluoromethyl)-1H-1,2,3-triazole,
5-Iodo-1-(pentafluoroethyl)-4-phenyl-1H-1,2,3-triazole and
4-Phenyl-1-(1,1,2,2-tetrafluoro-2-(phenylthio)ethyl)-1H-1,2,3-triazole.

These compounds are useful as starting compounds for production of medicaments, biologically active materials, and agrochemicals, or as components of medicaments, biologically active materials, and agrochemicals.

EXAMPLES

List of Abbreviations

Ac acetyl
br.s. broad signal
d doublet
DMF dimethylformamide
EI electron impact ionization
ESI electrospray ionization
Et ethyl
HRMS high resolution mass spectroscopy
IR infrared spectroscopy
m multiplet
[M]+ molecular ion
m.p. melting point
Nf nonaflyl, nonafluorobutansulfonyl
NMR nuclear magnetic resonance
q quartet
rt room temperature
$R_f$ retention factor
s singlet
t triplet
THF tetrahydrofuran
TMS trimethylsilyl
Tos p-toluenesulfonyl The subject-matter of the present invention is further illustrated by the following examples, which should not be construed as not limiting the scope of the invention.

Example 1: Azidotrifluoromethane

In a two-neck round-bottom flask, CsF (3.65 g, 24 mmol) was dried under high vacuum overnight at 120° C. The flask was then cooled to rt and filled with argon. Dry DMF (44 mL) was added, the reaction mixture was stirred and cooled to −60° C. A cold solution of $CF_3TMS$ (3.55 mL, 24 mmol) and $TosN_3$ (3.07 mL, 20 mmol) in dry DMF (6 mL) was added dropwise over 20 min and then the solution was stirred at −60° C. to −30° C. over 4 h. Cold, dry THF (40 mL) was added and the product was distilled from the reaction mixture (bath temperature max. 120° C., normal pressure) to a flask cooled to −78° C. containing $PhCF_3$ as an internal standard. The product was obtained as a solution in THF containing TMSF as a side-product and traces of $CF_3H$. Yield 70-80% based on $^{19}F$ NMR. $^{13}C$ NMR (101 MHz, $CDCl_3$) δ=122.0 (q, $^1J_{C-F}$=267.6 Hz); $^{19}F$ NMR (376 MHz, $CDCl_3$) δ=−56.3 (s); HRMS (EI) m/z calculated for $CF_3N_3$ [M]+: 111.0044, found 111.0040.

Example 2: Azidoperfluoroethane

To a Schlenk flask filled with argon, dry THF (40 mL) was added. $C_2F_5H$ (1.71 g, 14.3 mmol) was introduced, the resulting solution was cooled to −78° C. and then a solution of n-BuLi (1.6 mol·l$^{-1}$, 8.9 mL, 14.3 mmol) in hexanes was added dropwise. The mixture was stirred at −78° C. for 30 min, the color changed from colorless to bright yellow. A solution of $TosN_3$ (2.2 mL, 14.3 mmol) in dry THF (9.5 mL) was added dropwise and a pink precipitate formed. The mixture was stirred for another 30 min at −78° C. and then the product was distilled together with THF at temperature up to 33° C. and pressure 120 torr to a flask cooled to −78° C. containing $PhCF_3$ as an internal standard. The product was obtained as a solution in THF. Yield 83% based on $^{19}F$ NMR. $^{13}C$ NMR (101 MHz, $CDCl_3$) δ=117.0 (qt, $^1J_{C-F}$=267.6 Hz, $^2J_{C-F}$=41.9 Hz, $CF_3$), 113.2 (tq, $^1J_{C-F}$=272.9 Hz, $^2J_{C-F}$=41.4 Hz, $CF_2$); $^{19}F$ NMR (376 MHz, $CDCl_3$) δ=−85.9 (s, 3F), −93.6 (s, 2F); HRMS (EI) m/z calculated for $C_2F_5N_3$ [M]+: 161.0012, found 161.0010.

Example 3:
1-Azido-1,1,2,2,3,3,3-heptafluoropropane

In a screw-cap vial, CsF (0.25 g, 1.66 mmol) was dried under high vacuum at 135° C. for 48 h. The vial was then cooled to ambient temperature and filled with argon. Dry DMF (1.0 mL) was added and the mixture was cooled to −60° C. A cold solution of n-$C_3F_7TMS$ (0.284 mL, 1.4 mmol) and $NfN_3$ (0.455 g, 1.4 mmol) in dry DMF (0.5 mL) was added over 10 min and then the mixture was stirred at −60° C. to −30° C. for 4 h. Cold and dry THF (2.0 mL) was added and the product was distilled from the reaction mixture (bath temperature max. 95° C.) to a flask cooled to −78° C. containing $PhCF_3$ as an internal standard. The product was obtained as a THF solution containing TMSF as a side-product. Yield 49-52% according to $^{19}F$ NMR. $^{13}C$ NMR (101 MHz, $CDCl_3$) δ=117.1 (qt, $^1J_{C-F}$=287.0 Hz, $^2J_{C-F}$=33.3 Hz, $CF_3$); 114.6 (tt, $^1J_{C-F}$=275.7 Hz, $^2J_{C-F}$=30.3 Hz, CF$_2$); 107.5 (tqt, $^1J_{C-F}$=267.7 Hz, $^2J_{C-F}$=39.4 Hz, $^3J_{C-F}$=11.1 Hz, CF$_2$); $^{19}$F NMR (376 MHz, CDCl$_3$) δ=−80.9 (s, 3F), −89.1 (s, 2F), −128.3 (s, 2F); HRMS (EI) m/z calculated for C$_3$F$_6$N$_3$ [M−F]$^+$: 191.9994, found 191.9996.

Example 4: 1-Azido-1,1,2,2,3,3,4,4,5,5,6,6,7,7,8,8,8-heptadecafluorooctane

In a screw-cap vial, CsF (0.25 g, 1.66 mmol) was dried under high vacuum at 135° C. for 48 h.

The vial was then cooled to ambient temperature and filled with argon. Dry DMF (1.0 mL) was added and the mixture was cooled to −60° C. A cold solution of n-C$_8$F$_{17}$TMS (0.474 mL, 1.4 mmol) in dry DMF (0.5 mL) was added dropwise over 10 min and the reaction mixture was degased (one freeze-thaw cycle). A solution of NfN$_3$ (0.455 g, 1.4 mmol) in dry DMF (0.5 mL) was added dropwise and the mixture was stirred from −60° C. to −30° C. for 4 h. Dry cold THF (2.0 mL) was added and the product was distilled from the reaction mixture together with THF (bath max. 90° C.) to a flask cooled to −78° C. containing PhCF$_3$ as an internal standard. The product was obtained as a solid, which at temperature lower than −60° C. separated from THF. Yield 50-60% according to $^{19}$F NMR. $^{13}$C NMR (101 MHz, CDCl$_3$) δ=117.1 (qt, $^1J_{C-F}$=311.1 Hz, $^2J_{C-F}$=32.3 Hz, CF$_3$); 115.9 (tt, $^1J_{C-F}$=292.9 Hz, $^2J_{C-F}$=33.3 Hz, CF$_2$ (1)); 113.5-105.1 (m, CF$_2$ (2-7)); $^{19}$F NMR (376 MHz, CDCl$_3$) δ=−81.3 (s, 3F), −88.6 (s, 2F), −121.6 (s, 2F), −122.4 (s, 2F), −123.2 (s, 2F), −124.4 (s, 2F), −126.3 (s, 2F), −126.6 (s, 2F). HRMS (EI) m/z calculated for C$_8$F$_{16}$N$_3$ [M−F]$^+$: 441.9837, found 441.9836.

Example 5: (2-Azido-1,1,2,2-tetrafluoroethyl)(phenyl)sulfane i-PrMgCl.LiCl (1.3 mol·l$^{-1}$, 0.52 mL, 0.675 mmol) was added dropwise to a solution of (2-bromo-1,1,2,2-tetrafluoroethyl)(phenyl)sulfane (150 mg, 0.52 mmol) in dry THF (2 mL) at −78° C. The mixture was stirred for 5 min under argon and then a solution of NfN$_3$ (0.337 g, 1.038 mmol) in THF (1 mL) was added. The reaction mixture was stirred at −78° C. for 20 min and then at rt for 18 h. A saturated aqueous solution of NH$_4$Cl (6 mL) was added, the product was extracted into Et$_2$O (3×10 mL), the combined organic phase was dried with MgSO$_4$ and evaporated under reduced pressure. Purification on column chromatography (silicagel) gave product as a colorless oil. Yield 53%; IR (CHCl$_3$, film) ν=2155, 1583, 1578, 1476, 1443, 1299, 1240, 1183, 1115, 1099, 1088, 1025, 892, 750, 690 cm$^{-1}$; $^1$H NMR (400 MHz, CDCl$_3$) δ=7.72-7.63 (m, 2H), 7.56-7.48 (m, 1H), 7.48-7.42 (m, 2H); $^{13}$C NMR (101 MHz, CDCl$_3$) δ=137.2, 130.9, 129.4, 123.3 (t, J$_{C-F}$=2.6 Hz), 122.5 (tt, $^1J_{C-F}$=290.5 Hz, $^2J_{C-F}$=39.1 Hz, CF$_2$), 116.4 (tt, $^1J_{C-F}$=274.3 Hz, $^2J_{C-F}$=34.2 Hz, CF$_2$); $^{19}$F NMR (376 MHz, CDCl$_3$) δ=−89.7 (t, $^2J_{F-F}$=7.4 Hz, 2F), −89.8 (t, $^2J_{F-F}$=7.4 Hz, 2F).

Example 6: 1-(2-Azido-1,1,2,2-tetrafluoroethoxy)-4-bromobenzene i-PrMgCl.LiCl (1.3 mol·l$^{-1}$, 0.46 mL, 0.60 mmol) was added dropwise to the solution of 1-bromo-4-(2-bromo-1,1,2,2-tetrafluoroethoxy)benzene (200 mg, 0.57 mmol) in dry THF (2 mL) at −78° C. The mixture was stirred for 5 min under argon and then a solution of NfN$_3$ (0.370 g, 1.14 mmol) in THF (1 mL) was added dropwise. The reaction mixture was stirred at −78° C. to 25° C. for 3 h. Saturated aqueous NH$_4$Cl (6 mL) was added, the product was extracted into Et$_2$O (3×10 mL), the combined organic phase was dried MgSO$_4$ and solvent removed under reduced pressure. Purification by column chromatography (silicagel) gave the product as a colorless oil. Yield 71%; R$_f$(hexane)= 0.85; IR (CHCl$_3$, film) ν=2962, 2928, 2158, 1484, 1356, 1296, 1192, 1165, 1110, 1069, 1027, 956, 825, 781 cm$^{-1}$; $^1$H NMR (300.13 MHz, CDCl$_3$) δ=7.11 (m, 2H), 7.52 (m, 2H); $^{13}$C NMR (75.48 MHz, CDCl$_3$) δ=114.2 (tt, $^1J_{C-F}$=272 Hz, $^2J_{C-F}$=40.0 Hz, CF$_2$), 116.0 (tt, $^1J_{C-F}$=276 Hz, $^2J_{C-F}$=38.5 Hz, CF$_2$), 120.2, 123.4 (t, $^4J_{C-F}$=0.9 Hz), 132.9, 147.7 (t, $^3J_{C-F}$=1.7 Hz); $^{19}$F NMR (282.38 MHz, CDCl$_3$) δ=−94.0 (t, $^3J_{F-F}$=2.7 Hz, 2F), −87.4 (t, $^3J_{F-F}$=2.7 Hz, 2F).

Example 7: 1-(Pentafluoroethyl)-4-phenyl-1H-1,2,3-triazole

To a 10 mL screw cap vial, phenylacetylene (0.5 mmol) and a solution of azidopentafluoroethane in THF (~0.60 mmol, 3-4 mL) were added. An aqueous solution of CuSO$_4$.5H$_2$O (1 mol·l$^{-1}$, 0.05 mmol, 50 μl) and sodium L-ascorbate (1 mol·l$^{-1}$, 0.05 mmol, 50 μl) were added, the vial was closed and the content was stirred at rt for 18 h. Saturated aqueous NH$_4$Cl (10 mL) was added and the product was extracted into CH$_2$Cl$_2$ (3×10 mL). The combined organic phase was washed with water (2×10 mL), dried (MgSO$_4$), filtered and solvent was removed under reduced pressure. Purification by column chromatography (silicagel) gave pure product as a white solid. Yield 84%; m.p. 82-83° C.; R$_f$ (cyklohexane:EtOAc 97:3)=0.28; IR (CHCl$_3$, film) ν=1216, 1172, 1120, 1075, 691 cm$^{-1}$; $^1$H NMR (400 MHz, CDCl$_3$) δ=8.13 (s, 1H), 7.90-7.86 (m, 2H), 7.51-7.46 (m, 2H), 7.45-7.40 (m, 1H); $^{13}$C NMR (101 MHz, CDCl$_3$) δ=148.9, 129.5, 129.2, 128.6, 126.3, 117.9, 117.2 (qt, $^1J_{C-F}$=287.6 Hz, $^2J_{C-F}$=41.3 Hz, CF$_3$), 110.4 (tq, $^1J_{C-F}$=270.9 Hz, $^2J_{C-F}$=43.1 Hz, CF$_2$); $^{19}$F NMR (376 MHz, CDCl$_3$) δ=−84.4 (s, 3F), −99.2 (s, 2F); HRMS (ESI) m/z calculated for C$_{10}$H$_7$N$_3$F$_5$ [M+H]$^+$: 264.0555, found 264.0555.

Example 8: 4-(4-Methoxyphenyl)-1-(pentafluoroethyl)-1H-1,2,3-triazole

To a 10 mL screw cap vial, 4-methoxyphenylacetylene (0.5 mmol) and a solution of azidopentafluoroethane in THF (~0.60 mmol, 3-4 mL) were added. An aqueous solution of CuSO$_4$.5H$_2$O (1 mol·l$^{-1}$, 0.05 mmol, 50 μl) and sodium L-ascorbate (1 mol·l$^{-1}$, 0.05 mmol, 50 μl) were added, the vial was closed and the content was stirred at rt for 18 h. Saturated aqueous NH$_4$Cl (10 mL) was added and the product was extracted into CH$_2$Cl$_2$ (3×10 mL).

The combined organic phase was washed with water (2×10 mL), dried (MgSO$_4$), filtered and solvent was removed under reduced pressure. Purification by column chromatography (silicagel) gave pure product as a white solid. Yield 63%; m.p. 100-102° C.; R$_f$ (cyklohexane:EtOAc, 95:5)=0.26; IR (CHCl$_3$, film) ν=1618, 1501, 1434, 1223, 1123, 536 cm$^{-1}$; $^1$H NMR (400 MHz, CDCl$_3$) δ=8.04 (s, 1H), 7.82-7.78 (m, 2H), 7.01-6.97 (m, 2H), 3.86 (s, 3H); $^{13}$C NMR (101 MHz, CDCl$_3$) δ=160.6, 148.7, 127.7, 121.2, 117.2 (qt, $^1J_{C-F}$=287.5 Hz, $^2J_{C-F}$=41.4 Hz, CF$_3$), 116.9, 114.6, 110.3 (tq, $^1J_{C-F}$=270.6 Hz, $^2J_{C-F}$=43.1 Hz, CF$_2$), 55.5; $^{19}$F NMR (376 MHz, CDCl$_3$) δ=−84.4 (s, 3F), −99.2 (s, 2F); HRMS (ESI) m/z calculated for C$_{11}$H$_9$ON$_3$F$_5$ [M+H]$^+$: 294.0660, found 294.0661.

Example 9: 4-(2-Bromophenyl)-1-(pentafluoroethyl)-1H-1,2,3-triazole

To a 10 mL screw cap vial, 2-bromophenylacetylene (0.5 mmol) and a solution of azidopentafluoroethane in THF (~0.60 mmol, 3-4 mL) were added. An aqueous solution of CuSO$_4$.5H$_2$O (1 mol·l$^{-1}$, 0.05 mmol, 50 μl) and sodium L-ascorbate (1 mol·l$^{-1}$, 0.05 mmol, 50 μl) were added, the vial was closed and the content was stirred at rt for 18 h. Saturated aqueous NH$_4$Cl (10 mL) was added and the product was extracted into CH$_2$Cl$_2$ (3×10 mL). The combined organic phase was washed with water (2×10 mL), dried (MgSO$_4$), filtered and solvent was removed under reduced pressure. Purification by column chromatography (silicagel) gave pure product as a white solid. Yield 37%; R$_f$ (cyklohexane:EtOAc 95:5)=0.53; IR (CHCl$_3$, film) ν=1430, 1210, 1128, 1077, 972 cm$^{-1}$; $^1$H NMR (400 MHz, CDCl$_3$) δ=8.63 (s, 1H), 8.15 (dd, J=7.8, 1.7 Hz, 1H), 7.70 (dd, J=8.1, 1.2 Hz, 1H), 7.47 (td, J=7.6, 1.3 Hz, 1H), 7.29 (td, 1H); $^{13}$C NMR (101 MHz, CDCl$_3$) δ=146.4, 133.9, 131.1, 130.6, 129.4, 128.1, 121.6, 121.4, 117.2 (qt, $^1J_{C-F}$=287.5 Hz, $^2J_{C-F}$=41.2 Hz, CF$_3$), 110.3 (tq, $^1J_{C-F}$=271.4 Hz, $^1J_{C-F}$=43.2 Hz, CF$_2$); $^{19}$F NMR (376 MHz, CDCl$_3$) δ=−84.4 (s, 3F), −99.2 (s, 2F); HRMS (ESI) m/z calculated for C$_{10}$H$_6$N$_3$BrF$_5$ [M+H]$^+$: 341.9660, found 341.9661.

Example 10: 3-(1-(Pentafluoroethyl)-1H-1,2,3-triazol-4-yl)pyridine

To a 10 mL screw cap vial, 3-pyridylacetylene (0.5 mmol) and a solution of azidopentafluoroethane in THF (~0.60 mmol, 3-4 mL) were added. An aqueous solution of CuSO$_4$.5H$_2$O (1 mol·l$^{-1}$, 0.05 mmol, 50 μl) and sodium L-ascorbate (1 mol·l$^{-1}$, 0.05 mmol, 50 μl) were added, the vial was closed and the content was stirred at rt for 18 h. Saturated aqueous NH$_4$Cl (10 mL) was added and the product was extracted into CH$_2$Cl$_2$ (3×10 mL). The combined organic phase was washed with water (2×10 mL), dried (MgSO$_4$), filtered and solvent was removed under reduced pressure. Purification by column chromatography (silicagel) gave pure product as a white solid. Yield 38%; m.p. 120-122° C.; R$_f$ (cyklohexane:EtOAc 1:1)=0.48; IR (CHCl$_3$, film) ν=1578, 1439, 1218, 1169, 1121, 1078 cm$^{-1}$; $^1$H NMR (400 MHz, CDCl$_3$) δ=9.09 (d, J=2.5 Hz, 1H), 8.68 (dd, J=4.9, 1.6 Hz, 1H), 8.29 (s, 1H), 8.27 (dt, J=8.0, 2.0 Hz, 1H), 7.45 (dd, J=8.0, 4.9 Hz, 1H); $^{13}$C NMR (101 MHz, CDCl$_3$) δ=150.5, 147.4, 145.9, 133.7, 124.9, 124.0, 118.5, 117.1 (qt, $^1J_{C-F}$=287.5 Hz, $^2J_{C-F}$=40.6 Hz, CF$_3$), 110.3 (tq, $^1J_{C-F}$=272.2 Hz, $^2J_{C-F}$=43.1 Hz, CF$_2$); $^{19}$F NMR (376 MHz, CDCl$_3$) δ=−84.3 (s, 3F), −99.1 (s, 2F); HRMS (ESI) m/z calculated for C$_9$H$_6$N$_4$F$_5$ [M+H+]: 265.0507, found 265.0508.

Example 11: 4-Phenyl-1-(trifluoromethyl)-1H-1,2,3-triazole

To a 10 mL screw cap vial, copper(I) 3-methylsalicylate (5.4 mg, 0.025 mmol), a cold (−20° C.) solution of azidotrifluoromethane in THF (~1.5 mmol, 3-4 mL) and a solution of phenylacetylene (1.0 mmol) in THF (0.5 mL) were added. The vial was closed and the content stirred at rt for 18 h. THF was removed under reduced pressure, Et$_2$O (20 mL) was added and the organic phase was washed with aqueous NaHCO$_3$ (5%, 2×10 mL), water (10 mL), aqueous LiCl (1 mol·l$^{-1}$, 10 mL) and brine (10 mL), dried (MgSO$_4$), filtered and solvent was removed under reduced pressure. Purification by column chromatography (silicagel) gave the product as a white solid. Yield 81%; m.p. 91-92° C.; R$_f$ (cyklohexane:EtOAc, 97:3)=0.27; IR (CHCl$_3$, film) ν=1430, 1205, 1006, 694 cm$^{-1}$; $^1$H NMR (400 MHz, CDCl$_3$) δ=8.14 (s, 1H), 7.89-7.86 (m, 2H), 7.50-7.46 (m, 2H), 7.44-7.40 (m, 1H); $^{13}$C NMR (101 MHz, CDCl$_3$) δ=148.6, 129.4, 129.2, 128.6, 126.2, 117.7 (q, $^1J_{C-F}$=267.7 Hz, CF$_3$), 117.3; $^{19}$F NMR (376 MHz, CDCl$_3$) δ=−59.3 (s); HRMS (EI) m/z calculated for C$_9$H$_6$N$_3$F$_3$ [M]$^+$: 213.0514, found 213.0520.

Example 12: 4-(p-Tolyl)-1-(trifluoromethyl)-1H-1,2,3-triazole

To a 10 mL screw cap vial, copper(I) 3-methylsalicylate (5.4 mg, 0.025 mmol), a cold (−20° C.) solution of azidotrifluoromethane in THF (~1.5 mmol, 3-4 mL) and a solution of 4-methylphenylacetylene (1.0 mmol) in THF (0.5 mL) were added. The vial was closed and the content stirred at rt for 18 h. THF was removed under reduced pressure, Et$_2$O (20 mL) was added and the organic phase was washed with aqueous NaHCO$_3$ (5%, 2×10 mL), water (10 mL), aqueous LiCl (1 mol·l$^{-1}$, 10 mL) and brine (10 mL), dried (MgSO$_4$), filtered and solvent was removed under reduced pressure. Purification by column chromatography (silicagel) gave the product as a white solid. Yield 79%; m.p. 99-101° C.; R$_f$ (cyklohexane:EtOAc, 97:3)=0.19; IR (CHCl$_3$, film)=1444, 1189, 1007, 814 cm$^{-1}$; $^1$H NMR (400 MHz, CDCl$_3$) δ=8.09 (s, 1H), 7.77-7.74 (m, 2H), 7.30-7.27 (m, 2H), 2.41 (s, 3H); $^{13}$C NMR (101 MHz, CDCl$_3$) δ=148.7, 139.5, 129.8, 126.1, 125.8, 117.7 (q, $^1J_{C-F}$=268.1 Hz, CF$_3$), 116.8, 21.4; $^{19}$F NMR (376 MHz, CDCl$_3$) δ=−59.3 (s); HRMS (ESI) m/z calculated for C$_{10}$H$_9$N$_3$F$_3$ [M+H]+: 228.0743, found 228.0742.

Example 13: 4-(4-Methoxyphenyl)-1-(trifluoromethyl)-1H-1,2,3-triazole

To a 10 mL screw cap vial, copper(I) 3-methylsalicylate (5.4 mg, 0.025 mmol), a cold (−20° C.) solution of azidotrifluoromethane in THF (~1.5 mmol, 3-4 mL) and a solution of 4-methoxyphenylacetylene (1.0 mmol) in THF (0.5 mL) were added. The vial was closed and the content stirred at rt for 18 h. THF was removed under reduced pressure, Et$_2$O (20 mL) was added and the organic phase was washed with aqueous NaHCO$_3$ (5%, 2×10 mL), water (10 mL), aqueous LiCl (1 mol·l$^{-1}$, 10 mL) and brine (10 mL), dried (MgSO$_4$), filtered and solvent was removed under reduced pressure. Purification by column chromatography (silicagel) gave the product as a white solid. Yield 79%; m.p. 112-115° C.; R$_f$ (cyklohexane:EtOAc, 97:3)=0.12; IR (CHCl$_3$, film)=1445, 1257, 1215, 1194, 828 cm$^{-1}$; $^1$H NMR (400 MHz, CDCl$_3$) δ=8.04 (s, 1H), 7.82-7.78 (m, 2H), 7.02-6.98 (m, 2H), 3.86 (s, 3H); $^{13}$C NMR (101 MHz, CDCl$_3$) δ=160.5, 148.5, 127.6, 121.2, 117.8 (q, $^1J_{C-F}$=268.0 Hz, CF$_3$), 116.3, 114.6, 55.5 (s); $^{19}$F NMR (376 MHz, CDCl$_3$) δ=−59.4 (s); HRMS (ESI) m/z calculated for C$_{10}$H$_9$N$_3$OF$_3$ [M+H]$^+$: 244.0692, found 244.0693.

Example 14: 4-(2-Bromophenyl)-1-(trifluoromethyl)-1H-1,2,3-triazole

To a 10 mL screw cap vial, copper(I) 3-methylsalicylate (5.4 mg, 0.025 mmol), a cold (−20° C.) solution of azidotrifluoromethane in THF (~1.5 mmol, 3-4 mL) and a solution of 2-bromophenylacetylene (1.0 mmol) in THF (0.5 mL) were added. The vial was closed and the content stirred at rt for 18 h. THF was removed under reduced pressure, Et$_2$O (20 mL) was added and the organic phase was washed with aqueous NaHCO$_3$ (5%, 2×10 mL), water (10 mL), aqueous LiCl (1 mol·l$^{-1}$, 10 mL) and brine (10 mL), dried (MgSO$_4$), filtered and solvent was removed under reduced pressure. Purification by column chromatography (silicagel) gave the product as a yellow oil. Yield 84%; R$_f$ (cyklohexane:EtOAc, 97:3)=0.27; IR (CHCl$_3$, film)=1420, 1206, 1191, 760 cm$^{-1}$; $^1$H NMR (400 MHz, CDCl$_3$) δ=8.63 (s, 1H), 8.16-8.14 (ddd, J=7.8, 1.7, 0.4 Hz, 1H), 7.71-7.69 (ddd, J=8.1, 1.3, 0.4 Hz, 1H), 7.49-7.45 (ddd, J=7.9, 7.4, 1.3 Hz, 1H), 7.31-7.27 (ddd, J=8.1, 7.4, 1.8 Hz, 1H); $^{13}$C NMR (101 MHz, CDCl$_3$) δ=146.1, 133.8, 131.0, 130.5, 129.4, 128.0, 121.4, 120.6, 117.7 (q, $^1J_{C-F}$=268.4 Hz); $^{19}$F NMR (376 MHz, CDCl$_3$) δ=-59.2 (s); HRMS (ESI) m/z calculated for C$_9$H$_6$N$_3$F$_3$Br [M+H]$^+$: 291.9692, found 291.9692.

Example 15: 4-(4-Nitrophenyl)-1-(trifluoromethyl)-1H-1,2,3-triazole

To a 10 mL screw cap vial, copper(I) 3-methylsalicylate (5.4 mg, 0.025 mmol), a cold (-20° C.) solution of azidotrifluoromethane in THF (~1.5 mmol, 3-4 mL) and a solution of 2-nitrophenylacetylene (1.0 mmol) in THF (0.5 mL) were added. The vial was closed and the content stirred at rt for 18 h. THF was removed under reduced pressure, Et$_2$O (20 mL) was added and the organic phase was washed with aqueous NaHCO$_3$ (5%, 2×10 mL), water (10 mL), aqueous LiCl (1 mol·l$^{-1}$, 10 mL) and brine (10 mL), dried (MgSO$_4$), filtered and solvent was removed under reduced pressure. Purification by column chromatography (silicagel) gave the product as a yellow solid. Yield 82%; m.p. 166-168° C.; R$_f$ (cyklohexane:EtOAc, 97:3)=0.25; IR (CHCl$_3$, film)=1518, 1350, 1217, 1002 cm$^{-1}$; $^1$H NMR (400 MHz, CDCl$_3$) δ=8.38-8.34 (m, 2H), 8.31 (s, 1H), 8.10-8.06 (m, 2H); $^{13}$C NMR (101 MHz, CDCl$_3$) δ=148.3, 146.4, 134.8, 127.0, 124.6, 118.9, 117.6 (q, $^1J_{C-F}$=269.1 Hz); $^{19}$F NMR (376 MHz, CDCl$_3$) δ=-59.3 (s); HRMS (CI) m/z calculated for C$_9$H$_6$N$_4$O$_2$F$_3$ [M+H]$^+$: 259.0437, found 259.0439.

Example 16: 4-(1-(Trifluoromethyl)-1H-1,2,3-triazol-4-yl)aniline

To a 10 mL screw cap vial, copper(I) 3-methylsalicylate (5.4 mg, 0.025 mmol), a cold (-20° C.) solution of azidotrifluoromethane in THF (~1.5 mmol, 3-4 mL) and a solution of 4-ethynylaniline (1.0 mmol) in THF (0.5 mL) were added. The vial was closed and the content stirred at rt for 18 h. THF was removed under reduced pressure, Et$_2$O (20 mL) was added and the organic phase was washed with aqueous NaHCO$_3$ (5%, 2×10 mL), water (10 mL), aqueous LiCl (1 mol·l$^{-1}$, 10 mL) and brine (10 mL), dried (MgSO$_4$), filtered and solvent was removed under reduced pressure. Purification by column chromatography (silicagel) gave the product as a yellow solid. Yield 76%; m.p. 104-106° C.; R$_f$ (cyklohexane:EtOAc:Et$_3$N, 80:19:1)=0.14; IR (CHCl$_3$, film) ν=3398, 3321, 1432, 1195, 819 cm$^{-1}$; $^1$H NMR (400 MHz, CDCl$_3$) δ=7.98 (s, 1H), 7.67-7.64 (m, 2H), 6.77-6.73 (m, 2H), 3.86 (br s, 2H); $^{13}$C NMR (101 MHz, CDCl$_3$) δ=149.0, 147.7, 127.5, 118.7, 117.7 (q, $^1J_{C-F}$=267.7 Hz), 115.6, 115.2; $^{19}$F NMR (376 MHz, CDCl$_3$) δ=-59.4 (s); HRMS (ESI) m/z calculated for C$_9$H$_8$N$_4$F$_3$ [M+H]$^+$: 229.0696, found 229.0696.

Example 17: 4-Butyl-1-(trifluoromethyl)-1H-1,2,3-triazole

To a 10 mL screw cap vial, copper(I) 3-methylsalicylate (5.4 mg, 0.025 mmol), a cold (-20° C.) solution of azidotrifluoromethane in THF (~1.5 mmol, 3-4 mL) and a solution of hex-1-yne (1.0 mmol) in THF (0.5 mL) were added. The vial was closed and the content stirred at rt for 18 h. THF was removed under reduced pressure, Et$_2$O (20 mL) was added and the organic phase was washed with aqueous NaHCO$_3$ (5%, 2×10 mL), water (10 mL), aqueous LiCl (1 mol·l$^{-1}$, 10 mL) and brine (10 mL), dried (MgSO$_4$), filtered and solvent was removed under reduced pressure. Purification by column chromatography (silicagel) gave the product as a yellow oil. Yield 24%; R$_f$ (cyklohexane:EtOAc, 80:19:1)=0.17; IR (CHCl$_3$, film) ν=2938, 1382, 1194, 974 cm$^{-1}$; $^1$H NMR (400 MHz, CDCl$_3$) δ=7.69 (s, 1H), 2.79 (d, J=7.7 Hz, 2H), 1.70 (dt, J=15.4, 7.5 Hz, 2H), 1.41 (dq, J=14.7, 7.4 Hz, 2H), 0.95 (t, J=7.4 Hz, 3H); $^{13}$C NMR (101 MHz, CDCl$_3$) δ=149.4, 118.5, 117.7 (q, $^1J_{C-F}$=267.3 Hz), 31.1, 25.0, 22.3, 13.8; $^{19}$F NMR (376 MHz, CDCl$_3$) δ=-59.4 (s); HRMS (EI) m/z calculated for C$_7$H$_{10}$N$_3$F$_3$ [M]$^+$: 193.0827, found 193.0828.

Example 18: Ethyl 1-(trifluoromethyl)-1H-1,2,3-triazole-4-carboxylate

To a 10 mL screw cap vial, copper(I) 3-methylsalicylate (5.4 mg, 0.025 mmol), a cold (-20° C.) solution of azidotrifluoromethane in THF (~1.5 mmol, 3-4 mL) and a solution of ethyl propiolate (1.0 mmol) in THF (0.5 mL) were added. The vial was closed and the content stirred at rt for 18 h. THF was removed under reduced pressure, Et$_2$O (20 mL) was added and the organic phase was washed with aqueous NaHCO$_3$ (5%, 2×10 mL), water (10 mL), aqueous LiCl (1 mol·l$^{-1}$, 10 mL) and brine (10 mL), dried (MgSO$_4$), filtered and solvent was removed under reduced pressure. Purification by column chromatography (silicagel) gave the product as a yellow oil. Yield 48%; R$_f$ (cyklohexane:EtOAc, 95:5)= 0.12; IR (CHCl$_3$, film) ν=1744, 1444, 1266, 1222 cm$^{-1}$; $^1$H NMR (400 MHz, CDCl$_3$) δ=8.53 (s, 1H), 4.48 (q, J=7.1 Hz, 2H), 1.43 (t, J=7.1 Hz, 3H); $^{13}$C NMR (101 MHz, CDCl$_3$) δ=159.3, 140.9, 125.8, 117.4 (q, $^1J_{C-F}$=269.8 Hz), 62.2, 14.3; $^{19}$F NMR (376 MHz, CDCl$_3$) δ=-59.3 (s); HRMS (ESI) m/z vypočteno pro C$_6$H$_7$N$_3$O$_2$F$_3$ [M+H]$^+$: 210.0485, nalezeno 210.0485, calculated for C$_6$H$_6$N$_3$O$_2$F$_3$Na [M+Na]$^+$: 232.0304, found 232.0304.

Example 19: 2-(1-(Trifluoromethyl)-1H-1,2,3-triazol-4-yl)propan-2-ol

To a 10 mL screw cap vial, copper(I) 3-methylsalicylate (5.4 mg, 0.025 mmol), a cold (-20° C.) solution of azidotrifluoromethane in THF (~1.5 mmol, 3-4 mL) and a solution of 2-methylbut-3-yn-2-ol (1.0 mmol) in THF (0.5 mL) were added. The vial was closed and the content stirred at rt for 18 h. THF was removed under reduced pressure, Et$_2$O (20 mL) was added and the organic phase was washed with aqueous NaHCO$_3$ (5%, 2×10 mL), water (10 mL), aqueous LiCl (1 mol·l$^{-1}$, 10 mL) and brine (10 mL), dried (MgSO$_4$), filtered and solvent was removed under reduced pressure. Purification by column chromatography (silicagel) gave the product as a white solid. Yield 74%; m.p. 42-43° C.; R$_f$ (cyklohexane:EtOAc, 70:30)=0.21; IR (CHCl$_3$, film) ν=3401, 1435, 1191, 982 cm$^{-1}$; $^1$H NMR (400 MHz, CDCl$_3$) δ=7.90 (s, 1H), 2.9 (s, 1H), 1.69 (s, 6H); $^{13}$C NMR (101 MHz, CDCl$_3$) δ=156.8, 118.7, 117.9, 117.7 (q, $^1J_{C-F}$=268.2 Hz), 68.7, 30.4; $^{19}$F NMR (376 MHz, CDCl$_3$) δ=-59.3 (s); HRMS (EI) m/z calculated for C$_6$H$_8$N$_3$OF$_3$Na [M+Na]$^+$: 218.0512, found 218.0511.

Example 20: (S)-4-(2-(Benzyloxy)propyl)-1-(trifluoromethyl)-1H-1,2,3-triazole To a 10 mL screw cap vial, copper(I) 3-methylsalicylate (5.4 mg, 0.025 mmol), a cold (−20° C.) solution of azidotrifluoromethane in THF (~1.5 mmol, 3-4 mL) and a solution of (S)-((pent-4-yn-2-yloxy)methyl)benzene (1.0 mmol) in THF (0.5 mL) were added. The vial was closed and the content stirred at rt for 18 h. THF was removed under reduced pressure, Et$_2$O (20 mL) was added and the organic phase was washed with aqueous NaHCO$_3$ (5%, 2×10 mL), water (10 mL), aqueous LiCl (1 mol·l$^{-1}$, 10 mL) and brine (10 mL), dried (MgSO$_4$), filtered and solvent was removed under reduced pressure. Purification by column chromatography (silicagel) gave the product as a pale yellow oil. Yield 90%; R$_f$ (cyklohexane:EtOAc, 95:5)=0.09; IR (CHCl$_3$, film) ν=1440, 1278, 1207, 980 cm$^{-1}$; $^1$H NMR (400 MHz, CDCl$_3$) δ=7.71 (s, 1H), 7.34-7.27 (m, 3H), 7.26-7.22 (m, 2H), 4.61 (d, J=11.6 Hz, 1H), 4.41 (d, J=11.6 Hz, 1H), 3.92-3.85 (m, 1H), 3.02 (dd, J=15.0, 4.7 Hz, 1H), 2.96 (dd, J=15.0, 7.0 Hz, 1H), 1.28 (d, J=6.1 Hz, 3H); $^{13}$C NMR (101 MHz, CDCl$_3$) δ=145.9, 138.4, 128.5, 127.8, 120.3, 117.7 (q, $^1J_{C-F}$=267.9 Hz), 73.6, 70.8, 32.8, 19.5; $^{19}$F NMR (376 MHz, CDCl$_3$) δ=−59.4 (s); HRMS (ESI) m/z calculated for C$_{13}$H$_{15}$N$_3$OF$_3$ [M+H]+: 286.1162, nalezeno 286.1162, calculated for [M+Na]$^+$: 308.0981, found 308.0983.

Example 21: 1-(Pentafluoroethyl)-4-(p-tolyl)-1H-1,2,3-triazole

To a 10 mL screw cap vial, copper(I) 3-methylsalicylate (5.4 mg, 0.025 mmol), a cold (−20° C.) solution of azidopentafluoroethane in THF (~1.5 mmol, 3-4 mL) and a solution of p-tolylacetylene (1.0 mmol) in THF (0.5 mL) were added. The vial was closed and the content stirred at rt for 18 h. THF was removed under reduced pressure, Et$_2$O (20 mL) was added and the organic phase was washed with aqueous NaHCO$_3$ (5%, 2×10 mL), water (10 mL), aqueous LiCl (1 mol·l$^{-1}$, 10 mL) and brine (10 mL), dried (MgSO$_4$), filtered and solvent was removed under reduced pressure. Purification by column chromatography (silicagel) gave the product as a white solid. Yield 88%; m.p. 92-94° C.; IR (CHCl$_3$, film) ν=1219, 1175, 1122, 1075, 736 cm$^{-1}$; $^1$H NMR (400 MHz, CDCl$_3$) δ=8.09 (s, 1H), 7.77-7.74 (m, 2H), 7.30-7.27 (m, 2H), 2.41 (s, 3H); $^{13}$C NMR (101 MHz, CDCl$_3$) δ=149.0, 139.6, 129.9, 126.2, 125.8, 117.5, 117.2 (qt, $^1J_{C-F}$=287.9 Hz, $^2J_{C-F}$=41.4 Hz, CF$_3$), 110.3 (tq, $^1J_{C-F}$=270.7 Hz, $^2J_{C-F}$=41.4 Hz, CF$_2$), 21.5; $^{19}$F NMR (376 MHz, CDCl$_3$) δ=−84.4 (s, 3F), −99.2 (s, 2F); HRMS (EI$^+$) m/z calculated for C$_{11}$H$_8$N$_3$F$_5$ [M]$^+$: 277.0638, found 277.0639.

Example 22: 4-(1-(Pentafluoroethyl)-1H-1,2,3-triazol-4-yl)aniline

To a 10 mL screw cap vial, copper(I) 3-methylsalicylate (5.4 mg, 0.025 mmol), a cold (−20° C.) solution of azidopentafluoroethane in THF (~1.5 mmol, 3-4 mL) and a solution of 4-ethynylaniline (1.0 mmol) in THF (0.5 mL) were added. The vial was closed and the content stirred at rt for 18 h. THF was removed under reduced pressure, Et$_2$O (20 mL) was added and the organic phase was washed with aqueous NaHCO$_3$ (5%, 2×10 mL), water (10 mL), aqueous LiCl (1 mol·l$^{-1}$, 10 mL) and brine (10 mL), dried (MgSO$_4$), filtered and solvent was removed under reduced pressure. Purification by column chromatography (silicagel) gave the product as a yellow solid. Yield 97%; m.p. 86-89° C.; IR (CHCl$_3$, film) ν=1625, 1353, 1217, 1185, 1123, 1074, 755 cm$^{-1}$; $^1$H NMR (400 MHz, CDCl$_3$) δ=8.00 (s, 1H), 7.70-7.68 (m, 2H), 6.79-6.77 (m, 2H), 3.92 (br s, 2H); $^{13}$C NMR (101 MHz, CDCl$_3$) δ=149.2, 147.6, 127.6, 118.7, 117.4 (qt, $^1J_{C-F}$=287.3 Hz, $^2J_{C-F}$=41.5 Hz, CF$_3$), 116.0, 115.4, 110.3 (tq, $^1J_{C-F}$=270.1 Hz, $^2J_{C-F}$=42.8 Hz, CF$_2$); $^{19}$F NMR (376 MHz, CDCl$_3$) δ=−84.4 (s, 3F), −99.2 (s, 2F); HRMS (ESI) m/z calculated for C$_{10}$H$_8$N$_4$F$_5$ [M+H]$^+$: 279.06636, found 279.06641.

Example 23: 1-(Pentafluoroethyl)-4-(4-(trifluoromethyl)phenyl)-1H-1,2,3-triazole To a 10 mL screw cap vial, copper(I) 3-methylsalicylate (5.4 mg, 0.025 mmol), a cold (−20° C.) solution of azidopentafluoroethane in THF (~1.5 mmol, 3-4 mL) and a solution of (4-trifluoromethyl)phenylacetylene (1.0 mmol) in THF (0.5 mL) were added. The vial was closed and the content stirred at rt for 18 h. THF was removed under reduced pressure, Et$_2$O (20 mL) was added and the organic phase was washed with aqueous NaHCO$_3$ (5%, 2×10 mL), water (10 mL), aqueous LiCl (1 mol·l$^{-1}$, 10 mL) and brine (10 mL), dried (MgSO$_4$), filtered and solvent was removed under reduced pressure. Purification by column chromatography (silicagel) gave the product as a white solid. Yield 91%; m.p. 121-124° C.; IR (CHCl$_3$, film) ν=1329, 1218, 1130, 1065, 747 cm$^{-1}$; $^1$H NMR (400 MHz, CDCl$_3$) δ=8.24 (s, 1H), 8.02-8.00 (m, 2H), 7.75-7.73 (m, 2H); $^{13}$C NMR (101 MHz, CDCl$_3$) δ=147.5, 132.0, 131.5 (q, $^2J_{C-F}$=33.3 Hz), 126.6, 126.3 (q, $^3J_{C-F}$=3.0 Hz), 124.0 (q, $^1J_{C-F}$=272.7 Hz, CF$_3$), 118.8, 117.1 (qt, $^1J_{C-F}$=287.9 Hz, $^2J_{C-F}$=41.4 Hz, CF$_3$), 110.3 (tq, $^1J_{C-F}$=271.7 Hz, $^2J_{C-F}$=43.4 Hz, CF$_2$); $^{19}$F NMR (376 MHz, CDCl$_3$) δ=−63.3 (s, 3F), −84.4 (s, 3F), −99.2 (s, 2F); HRMS (ESI) m/z calculated for C$_{11}$H$_8$N$_3$F$_8$ [M]$^+$: 331.0356, found 331.0350.

Example 24: 1-(Perfluoropropyl)-4-phenyl-1H-1,2,3-triazole

To a 10 mL screw cap vial, copper(I) 3-methylsalicylate (5.4 mg, 0.025 mmol), a cold (−20° C.) solution of 1-azido-1,1,2,2,3,3,3-heptafluoropropane in THF (~1.5 mmol, 3-4 mL) and a solution of phenylacetylene (1.0 mmol) in THF (0.5 mL) were added. The vial was closed and the content stirred at rt for 18 h. THF was removed under reduced pressure, Et$_2$O (20 mL) was added and the organic phase was washed with aqueous NaHCO$_3$ (5%, 2×10 mL), water (10 mL), aqueous LiCl (1 mol·l$^{-1}$, 10 mL) and brine (10 mL), dried (MgSO$_4$), filtered and solvent was removed under reduced pressure. Purification by column chromatography (silicagel) gave the product as a white solid. Yield 41%; m.p. 72-74° C.; IR (CHCl$_3$, film) ν=1423, 1226, 1196, 1137, 1051, 883, 694 cm$^{-1}$; $^1$H NMR (500 MHz, CDCl$_3$) δ=8.12 (s, 1H), 7.89-7.87 (m, 2H), 7.50-7.46 (m, 2H), 7.44-7.40 (m, 1H); $^{13}$C NMR (125.7 MHz, CDCl$_3$) δ=148.9, 129.6, 129.3, 128.6, 126.3, 118.1, 117.4 (qt, $^1J_{C-F}$=295.4 Hz, $^2J_{C-F}$=32.7 Hz, CF$_3$); 112.0 (tt, $^1J_{C-F}$=272.8 Hz, $^2J_{C-F}$=32.7 Hz, CF$_2$); 107.6 (tq, $^1J_{C-F}$=264.0 Hz, $^2J_{C-F}$=40.2 Hz, CF$_2$); $^{19}$F NMR (376 MHz, CDCl$_3$) δ=−81.0 (s, 3F), −96.5 (s, 2F), −127.6 (s, 2F); HRMS (EI) m/z calculated for C$_{11}$H$_6$N$_3$F$_7$ [M]$^+$: 313.0450, found 313.0445.

Example 25: 1-(Perfluorooctyl)-4-phenyl-1H-1,2,3-triazole

To a 10 mL screw cap vial, copper(I) 3-methylsalicylate (5.4 mg, 0.025 mmol), a cold (−20° C.) solution of 1-azido- 1,1,2,2,3,3,4,4,5,5,6,6,7,7,8,8,8-heptadecafluorooctane in THF (~1.5 mmol, 3-4 mL) and a solution of phenylacetylene (1.0 mmol) in THF (0.5 mL) were added.

The vial was closed and the content stirred at rt for 18 h. THF was removed under reduced pressure, Et$_2$O (20 mL) was added and the organic phase was washed with aqueous NaHCO$_3$ (5%, 2×10 mL), water (10 mL), aqueous LiCl (1 mol·l$^{-1}$, 10 mL) and brine (10 mL), dried (MgSO$_4$), filtered and solvent was removed under reduced pressure. Purification by column chromatography (silicagel) gave the product as a white solid. Yield 57%; m.p. 132-133° C.; IR (CHCl$_3$, film) ν=1218, 1151, 749, 671 cm$^{-1}$; $^1$H NMR (500 MHz, CDCl$_3$) δ=8.11 (s, 1H), 7.89-7.87 (m, 2H), 7.50-7.47 (m, 2H), 7.44-7.41 (m, 1H); $^{13}$C NMR (125.7 MHz, CDCl$_3$) δ=148.8, 129.6, 129.3, 128.6, 126.3, 118.1, 117.2, 112.5, 110.9, 110.82, 110.79, 110.3, 109.8, 108.5; $^{19}$F NMR (470.4 MHz, CDCl$_3$) δ=−81.2 (t, $^3J_{F-F}$=9.9 Hz, CF$_3$), −95.6 (t, $^3J_{F-F}$=11.0 Hz, CF$_2$), −121.7 to −122.9 (m, 3×CF$_2$), −123.0 to −123.3 (m, 2×CF$_2$), −126.6 (br s, CF$_2$); HRMS (EI) m/z calculated for C$_{16}$H$_7$N$_3$F$_{17}$ [M]$^+$: 564.03630, found 564.03631.

Example 26: 1-(Perfluoropropyl)-4-(p-tolyl)-1H-1,2,3-triazole

To a 10 mL screw cap vial, copper(I) 3-methylsalicylate (5.4 mg, 0.025 mmol), a cold (−20° C.) solution of 1-azido-1,1,2,2,3,3,3-heptafluoropropane in THF (~1.5 mmol, 3-4 mL) and a solution of p-tolylacetylene (1.0 mmol) in THF (0.5 mL) were added. The vial was closed and the content stirred at rt for 18 h. THF was removed under reduced pressure, Et$_2$O (20 mL) was added and the organic phase was washed with aqueous NaHCO$_3$ (5%, 2×10 mL), water (10 mL), aqueous LiCl (1 mol·l$^{-1}$, 10 mL) and brine (10 mL), dried (MgSO$_4$), filtered and solvent was removed under reduced pressure. Purification by column chromatography (silicagel) gave the product as a white solid. Yield 41%; m.p. 86-88° C.; IR (CHCl$_3$, film) ν=1236, 1139, 882, 750, 671 cm$^{-1}$; $^1$H NMR (400 MHz, CDCl$_3$) δ=8.08 (s, 1H), 7.78-7.76 (m, 2H), 7.29-7.27 (m, 2H), 2.41 (s, 1H); $^{13}$C NMR (101.0 MHz, CDCl$_3$) δ=148.9, 129.6, 139.6, 129.9, 126.2, 125.8, 117.7, 117.4 (qt, $^1J_{C-F}$=287.9 Hz, $^2J_{C-F}$=28.3 Hz, CF$_3$); 112.0 (tt, $^1J_{C-F}$=273.7 Hz, $^2J_{C-F}$=32.3 Hz, CF$_2$); 107.6 (tq, $^1J_{C-F}$=269.7 Hz, $^2J_{C-F}$=40.4 Hz, CF$_2$), 21.5; $^{19}$F NMR (376 MHz, CDCl$_3$) δ=−81.0 (s, 3F), −96.5 (s, 2F), −127.7 (s, 2F); HRMS (EI) m/z calculated for C$_{12}$H$_9$N$_3$F$_7$ [M+H]$^+$: 328.06792, found 328.06807.

Example 27: 4-(4-Methoxyphenyl)-1-(perfluorooctyl)-1H-1,2,3-triazole

To a 10 mL screw cap vial, copper(I) 3-methylsalicylate (5.4 mg, 0.025 mmol), a cold (−20° C.) solution of 1-azido-1,1,2,2,3,3,4,4,5,5,6,6,7,7,8,8,8-heptadecafluorooctane in THF (~1.5 mmol, 3-4 mL) and a solution of 4-methoxyphenylacetylene (1.0 mmol) in THF (0.5 mL) were added. The vial was closed and the content stirred at rt for 18 h. THF was removed under reduced pressure, Et$_2$O (20 mL) was added and the organic phase was washed with aqueous NaHCO$_3$ (5%, 2×10 mL), water (10 mL), aqueous LiCl (1 mol·l$^{-1}$, 10 mL) and brine (10 mL), dried (MgSO$_4$), filtered and solvent was removed under reduced pressure. Purification by column chromatography (silicagel) gave the product as a white solid. Yield 77%; m.p. 159-160° C.; IR (CHCl$_3$, film) ν=1218, 746, 670 cm$^{-1}$; $^1$H NMR (500 MHz, CDCl$_3$) δ=8.02 (s, 1H), 7.82-7.80 (m, 2H), 7.01-6.99 (m, 2H), 3.87 (s, 3H); $^{13}$C NMR (125.7 MHz, CDCl$_3$) δ=160.6, 148.7, 127.7, 121.2, 117.2, 117.1, 114.5, 112.5, 110.9, 110.82, 110.79, 110.3, 109.8, 108.5, 55.5; $^{19}$F NMR (470.4 MHz, CDCl$_3$) δ=−81.2 (t, $^3J_{F-F}$=9.9 Hz, CF$_3$), −95.6 (t, $^3J_{F-F}$=11.6 Hz, CF$_2$), −122.0 to −122.5 (m, 3×CF$_2$), −123.0 to −123.3 (m, 2×CF$_2$), −126.6 (br s, CF$_2$); HRMS (EI) m/z calculated for C$_{17}$H$_{90}$N$_3$F$_7$ [M+H]$^+$: 594.04687, found 594.04695.

Example 28: 1-(Trifluoromethyl)-4-(4-(trifluoromethyl)phenyl)-1H-1,2,3-triazole (Two-Step One Pot Synthesis)

CsF (182 mg, 1.2 mmol) was dried in a screw-cap vial overnight under high vacuum at 120° C. Then the vial was cooled to rt, filled with argon, dry DMF (4 mL) was added and the mixture was cooled to −60° C. A solution of CF$_3$TMS (177 μl, 1.2 mmol) and TosN$_3$ (153 μl, 1.0 mmol) in dry DMF (1 mL) was added dropwise and the mixture was stirred at −60° C. to −30° C. for 4 h. A solution of (4-trifluoromethyl)phenylacetylene (1.2 mmol) in dry DMF (0.5 mL) and an aqueous solution of CuSO$_4$.5H$_2$O (1 mol·l$^{-1}$, 0.12 mmol, 120 μl) and sodium L-ascorbate (1 mol·l$^{-1}$, 0.12 mmol, 120 μl) were added. The vial was closed and stirred at rt for 18 h. Water (5 mL) was added, the product was extracted into Et$_2$O (3×5 mL), the combined organic phase was washed with water (5 mL), aqueous LiCl (1 mol·l$^{-1}$, 2×5 mL), water (5 mL), dried (MgSO$_4$), filtered and solvent was removed under reduced pressure. Purification by column chromatography (silicagel) gave the product as a white solid. Yield 50%, m.p. 112-115° C., R$_f$ (cyklohexane:EtOAc 97:3)=0.18; IR (CHCl$_3$, film) ν=1444, 1223, 1204, 1109, 827 cm$^{-1}$; $^1$H NMR (400 MHz, CDCl$_3$) δ=8.23 (s, 1H), 8.00 (d, J=8.0 Hz, 2H), 7.73 (d, J=8.1 Hz, 2H); $^{13}$C NMR (101 MHz, CDCl$_3$) δ=147.2, 132.1, 131.4 (q, $^2J_{C-F}$=32.8 Hz, C—CF$_3$), 126.5, 126.3 (q, $^3J_{C-F}$=3.7 Hz, C=C—CF$_3$), 124.0 (q, $^1J_{C-F}$=272.1 Hz, C—CF$_3$), 118.2, 117.7 (q, $^1J_{C-F}$=268.7 Hz, N—CF$_3$); $^{19}$F NMR (376 MHz, CDCl$_3$) δ=−59.3 (s, 3F, N—CF$_3$), −63.3 (s, 3F, ArCF$_3$); HRMS (EI) m/z calculated for C$_{10}$H$_5$N$_3$F$_6$ [M]$^+$: 281.0388, found 281.0391.

Example 29: 4-(4-Fluorophenyl)-1-(trifluoromethyl)-1H-1,2,3-triazole (Two-Step One Pot Synthesis)

CsF (182 mg, 1.2 mmol) was dried in a screw-cap vial overnight under high vacuum at 120° C. Then the vial was cooled to rt, filled with argon, dry DMF (4 mL) was added and the mixture was cooled to −60° C. A solution of CF$_3$TMS (177 μl, 1.2 mmol) and TosN$_3$ (153 μl, 1.0 mmol) in dry DMF (1 mL) was added dropwise and the mixture was stirred at −60° C. to −30° C. for 4 h. A solution of 4-fluorophenylacetylene (1.2 mmol) in dry DMF (0.5 mL) and an aqueous solution of CuSO$_4$.5H$_2$O (1 mol·l$^{-1}$, 0.12 mmol, 120 μl) and sodium L-ascorbate (1 mol·l$^{-1}$, 0.12 mmol, 120 μl) were added. The vial was closed and stirred at rt for 18 h. Water (5 mL) was added, the product was extracted into Et$_2$O (3×5 mL), the combined organic phase was washed with water (5 mL), aqueous LiCl (1 mol·l$^{-1}$, 2×5 mL), water (5 mL), dried (MgSO$_4$), filtered and solvent was removed under reduced pressure. Purification by column chromatography (silicagel) gave the product as a white solid. Yield 81%, m.p. 110-111° C., R$_f$ (cyklohexane:EtOAc 97:3)=0.13; IR (CHCl$_3$, film) ν=1444, 1207, 1011, 823 cm$^{-1}$; $^1$H NMR (400 MHz, CDCl$_3$) δ=8.14 (s, 1H), 7.88-7.83 (m, 2H), 7.19-7.13 (m, 2H); $^{13}$C NMR (101 MHz, CDCl$_3$) δ=163.4 (d, $^1J_{C-F}$=249.3 Hz), 147.7, 128.2 (d, $^3J_{C-F}$=8.3 Hz), 124.9 (d, $^4J_{C-F}$=3.4 Hz), 117.7 (q, $^1J_{C-F}$=268.4 Hz), 117.0, 116.3 (d, $^2J_{C-F}$=15.1 Hz); $^{19}$F NMR (376 MHz, CDCl$_3$) δ=−59.3 (s, 3F), −111.9 (ddd, $J_{C-F}$=13.6, 8.5, 5.5 Hz, 1F); HRMS (EI) m/z calculated for C$_9$H$_5$N$_3$F$_4$ [M]$^+$: 231.0420, found 231.0410.

Example 30: 5-Iodo-1-(pentafluoroethyl)-4-phenyl-1H-1,2,3-triazole

A cooled (−20° C.) mixture of 1-azidopentafluoroethane in THF (2.7 mL, 0.64 mmol), and Et$_3$N (145 mg, 1.43 mmol) was added dropwise to a cooled mixture of copper(I) phenylacetylide (116 mg, 0.704 mmol) and iodine (164 mg, 0.64 mmol). The mixture was stirred in a closed vial at rt for 16 h. The mixture was then poured onto water (10 mL), extracted with Et$_2$O (3×10 mL), the combined organic phase was dried (MgSO$_4$), filtered and solvent was removed under reduced pressure. Purification by column chromatography (silicagel) gave the product as a white solid. Yield 60%, m.p. 119-120° C., $^1$H NMR (400 MHz, CDCl$_3$) δ=7.91-7.89 (m, 2H), 7.54-7.46 (m, 3H); $^{13}$C NMR (101 MHz, CDCl$_3$) δ=152.6, 129.7, 128.9, 128.6, 128.5, 117.2 (qt, $^1J_{C-F}$=288.8 Hz, $^2J_{C-F}$=38.4 Hz, CF$_3$), 112.2 (tq, $^1J_{C-F}$=271.7 Hz, $^2J_{C-F}$=43.4 Hz, CF$_2$), 71.4; $^{19}$F NMR (376 MHz, CDCl$_3$) δ=−81.4 (s, 3F), −93.4 (s, 2F); HRMS (EI) m/z calculated for C$_{10}$H$_6$N$_3$F$_5$I [M+H]$^+$: 389.95211, found 389.95225.

Example 31: 4-Phenyl-1-(1,1,2,2-tetrafluoro-2-(phenylthio)ethyl)-1H-1,2,3-triazole A mixture of (2-azido-1,1,2,2-tetrafluoroethyl)(phenyl)sulfane (83 mg, 0.33 mmol), phenylacetylene (33.7 mg, 0.33 mmol), CuSO$_4$.5H$_2$O (3 mg, 0.019 mmol), sodium L-ascorbate (6.5 mg, 0.03 mmol), tris((1-benzyl-1H-1,2,3-triazol-4-yl)methyl)amine (8.8 mg, 0.017 mmol), DMF (3 mL) and water (0.05 mL) was stirred in a closed vial in a microwave at 60° C. for 1 h. The mixture was then poured onto water (10 mL), extracted with Et$_2$O (3×10 mL), the combined organic phase was dried (MgSO$_4$), filtered and solvent was removed under reduced pressure. Purification by column chromatography (silicagel) gave the product as a white amorphous solid. Yield 81%, IR (CHCl$_3$, film) ν=3080, 3060, 1587, 1577, 1494, 1475, 1443, 1308, 1249, 1107, 1081, 1080, 1024, 965, 901, 838, 761, 691, 520 cm$^{-1}$; $^1$H NMR (400 MHz, CDCl$_3$) δ=8.04 (t, J=0.7 Hz, 1H), 7.88-7.82 (m, 2H), 7.66-7.60 (m, 2H), 7.49-7.42 (m, 3H), 7.42-7.35 (m, 3H); $^{13}$C NMR (101 MHz, CDCl$_3$) δ=148.33, 137.17, 131.07, 129.43, 129.10, 129.01, 128.89, 126.09, 122.67 (t, $^4J_{C-F}$=2.8 Hz), 122.02 (tt, $^1J_{C-F}$=291.6, $^2J_{C-F}$=39.2 Hz, CF$_2$), 118.25, 113.50 (tt, $^1J_{C-F}$=272.3, $^2J_{C-F}$=35.8 Hz, CF$_2$); $^{19}$F NMR (376 MHz, CDCl$_3$) δ=−89.61 (t, $^3J_{F-F}$=6.3 Hz), −95.56 (t, $^3J_{F-F}$=6.3 Hz); HRMS (EI) m/z calculated for C$_{16}$H$_{11}$F$_4$N$_3$S [M]$^+$: 353.0610, found 353.0613.

INDUSTRIAL APPLICABILITY

Compounds according to the invention can be used in the production of agrochemicals and biologically active compounds in pharmaceutical industry.

The invention claimed is:
1. A method for preparation of azidoperfluoroalkanes and azidopolyfluoroalkanes of formula R$_F$—N$_3$,
   wherein R$_F$ is selected from the group consisting of C$_n$F$_{2n+1}$, C$_n$F$_x$H$_{2n+1-x}$, C$_n$F$_x$X$_{2n+1-x}$ or R$^1$CF$_2$CF$_2$, wherein n is an integer in the interval from 1 to 10, x is an integer in the interval from 2 to 20 and
   X is Cl, Br, or I,
   R$^1$ is selected from the group consisting of C$_{1-10}$ alkyl, ArO, ArS, imidazolyl, benzimidazolyl, or pyrazolyl and Ar is phenyl or substituted phenyl,
said process having the following steps
(A) generation of a synthetic equivalent of polyfluoroalkyl carbanion, said synthetic equivalent having the formula [R$_F$]$^-$, by a method selected from:
a) activation of trialkyl(polyfluoroalkyl)silane of general formula R$^3$$_3$SiR$_F$, wherein R$^3$ is C$_{1-5}$ alkyl, with a Lewis base which is selected from the group consisting of potassium fluoride, cesium fluoride, tetramethylammonium fluoride, tetrabutylammonium fluoride, sodium carbonate, potassium carbonate, potassium phosphate, sodium acetate, potassium acetate, tetrabutylammonium acetate;
b) reaction of polyfluoroalkane of general formula R$_F$H with a base which is selected from a group consisting of methyllithium, butyllithium, phenyllithium, Grignard reagent of general formula R$^3$MgX, wherein R$^3$ is C$_{1-5}$ alkyl, and complexes of these compounds with LiCl; or
c) reaction of halopolyfluoroalkane of general formula R$_F$Br or R$_F$I with metalation reagents, which are selected from a group consisting of methyllithium, butyllithium, Grignard reagent of general formula R$^3$MgX, wherein R$^3$ is C$_{1-5}$ alkyl, and complexes of these compounds with LiCl,
at a temperature in the range from −78° C., or from the melting point of the reaction mixture, to +60° C., and
(B) reaction of an electrophilic azidation reagent of general formula R$^2$—N$_3$,
   wherein R$^2$ is selected from the group consisting of n-C$_4$F$_9$SO$_2$, ArSO$_2$, Br, and I, wherein Ar is phenyl or substituted phenyl,
with the synthetic equivalent of polyfluoroalkyl carbanion of general formula [R$_F$]$^-$ generated in step (A).
2. A method for preparation of N-perfluoroalkyl- or N-polyfluoroalkyl-substituted triazoles of formula 1

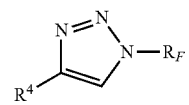

wherein R$_F$ is selected from the group consisting of C$_n$F$_{2n+1}$, C$_n$F$_x$H$_{2n+1-x}$, C$_n$F$_x$X$_{2n+1-x}$ or R$^1$CF$_2$CF$_2$, wherein n is an integer in the interval from 1 to 10, x is an integer in the interval from 2 to 20 and
X is Cl, Br, or I,
R$^1$ is selected from the group consisting of C$_{1-10}$ alkyl, ArO, ArS, imidazolyl, benzimidazolyl, or pyrazolyl and Ar is phenyl or substituted phenyl,
R$^4$ is selected from a group consisting of C$_{1-10}$ alkyl, XCH$_2$CH$_2$, COOR$^3$, C(CH$_3$)$_2$OH, benzyloxy-C$_{1-4}$-alkyl, pyridyl, phenyl, and pyridyl or phenyl substituted by a group selected from C$_{1-10}$ alkyl, F, Cl, Br, I, OR$^3$, NO$_2$, NH$_2$, CF$_3$, wherein R$^3$ is C$_{1-5}$ alkyl,
by performing the steps of:
(A) generation of a synthetic equivalent of polyfluoroalkyl carbanion, said synthetic equivalent having the formula [R$_F$]$^-$, by a method selected from:
a) activation of trialkyl(polyfluoroalkyl)silane of general formula R$^3$$_3$SiR$_F$, wherein R$^3$ is C$_{1-5}$ alkyl, with a Lewis base which is selected from the group consisting of potassium fluoride, cesium fluoride, tetramethylammonium fluoride, tetrabutylammonium fluoride, sodium carbonate, potassium carbonate, potassium phosphate, sodium acetate, potassium acetate, tetrabutylammonium acetate;
b) reaction of polyfluoroalkane of general formula $R_FH$ with a base which is selected from a group consisting of methyllithium, butyllithium, phenyllithium, Grignard reagent of general formula $R^3MgX$, wherein $R^3$ is $C_{1-5}$ alkyl, and complexes of these compounds with LiCl; or
c) reaction of halopolyfluoroalkane of general formula $R_FBr$ or $R_FI$ with metalation reagents, which are selected from a group consisting of methyllithium, butyllithium, Grignard reagent of general formula $R^3MgX$, wherein $R^3$ is $C_{1-5}$ alkyl, and complexes of these compounds with LiCl,
at a temperature in the range from −78° C., or from the melting point of the reaction mixture, to +60° C.,
and
(B) reaction of an electrophilic azidation reagent of general formula $R^2$—$N_3$,
wherein $R^2$ is selected from the group consisting of n-$C_4F_9SO_2$, $ArSO_2$, Br, and I, wherein Ar is phenyl or substituted phenyl,
with the synthetic equivalent of polyfluoroalkyl carbanion of general formula $[R_F]^-$ generated in step (A);
to obtain the azide $R_F$—$N_3$, and then
performing a cycloaddition reaction of the azide $R_F$—$N_3$ with alkyne of formula 2

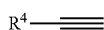

2 in the presence of copper(I) catalyst at a temperature in the range from −30° C. to the boiling point of the reaction mixture.

3. A method for preparation of compounds of general formula 3

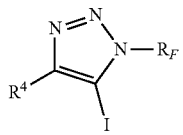

3 wherein $R_F$ is selected from the group consisting of $C_nF_{2n+1}$, $C_nF_xH_{2n+1-x}$, $C_nF_xX_{2n+1-x}$ or $R^1CF_2CF_2$, wherein n is an integer in the interval from 1 to 10, x is an integer in the interval from 2 to 20 and
X is Cl, Br, or I,
$R^1$ is selected from the group consisting of $C_{1-10}$ alkyl, ArO, ArS, imidazolyl, benzimidazolyl, or pyrazolyl and Ar is phenyl or substituted phenyl, $R^4$ is selected from a group consisting of $C_{1-10}$ alkyl, $XCH_2CH_2$, $COOR^3$, $C(CH_3)_2OH$, benzyloxy-$C_{1-4}$-alkyl, pyridyl, phenyl, and pyridyl or phenyl substituted by a group selected from $C_{1-10}$ alkyl, F, Cl, Br, I, $OR^3$, $NO_2$, $NH_2$, $CF_3$, wherein $R^3$ is $C_{1-5}$ alkyl,
by performing the steps of:
(A) generation of a synthetic equivalent of polyfluoroalkyl carbanion, said synthetic equivalent having the formula $[R_F]^-$, by a method selected from:
a) activation of trialkyl(polyfluoroalkyl)silane of general formula $R^3_3SiR_F$, wherein $R^3$ is $C_{1-5}$ alkyl, with a Lewis base which is selected from the group consisting of potassium fluoride, cesium fluoride, tetramethylammonium fluoride, tetrabutylammonium fluoride, sodium carbonate, potassium carbonate, potassium phosphate, sodium acetate, potassium acetate, tetrabutylammonium acetate;
b) reaction of polyfluoroalkane of general formula $R_FH$ with a base which is selected from a group consisting of methyllithium, butyllithium, phenyllithium, Grignard reagent of general formula $R^3MgX$, wherein $R^3$ is $C_{1-5}$ alkyl, and complexes of these compounds with LiCl; or
c) reaction of halopolyfluoroalkane of general formula $R_FBr$ or $R_FI$ with metalation reagents, which are selected from a group consisting of methyllithium, butyllithium, Grignard reagent of general formula $R^3MgX$, wherein $R^3$ is $C_{1-5}$ alkyl, and complexes of these compounds with LiCl,
at a temperature in the range from −78° C., or from the melting point of the reaction mixture, to +60° C.,
and
(B) reaction of an electrophilic azidation reagent of general formula $R^2$—$N_3$,
wherein $R^2$ is selected from the group consisting of n-$C_4F_9SO_2$, $ArSO_2$, Br, and I, wherein Ar is phenyl or substituted phenyl,
with the synthetic equivalent of polyfluoroalkyl carbanion of general formula $[R_F]^-$ generated in step (A);
to obtain the azide $R_F$—$N_3$, and then
performing a cycloaddition reaction of $R_F$—$N_3$ with alkyne of general formula 4

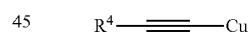

4 and with iodine in the presence of tertiary amine as a base, at a temperature in the range from −30° C. to the boiling point of the reaction mixture.

4. The method according to claim 3, wherein the tertiary amine is selected from trimethylamine, N,N-diisopropylethylamine, N,N,N',N'-tetramethylethylenediamine, tris((1-benzyl-1H-1,2,3-triazolyl)methyl)amine or tris((1-tert-butyl-1H-1,2,3-triazolyl)methyl)amine.

* * * * *